United States Patent [19]

Kaiser

[11] 4,250,099
[45] Feb. 10, 1981

[54] MEGASTIGMA-5(11), 8-DIEN-4,7-OXIDES AND TETRA-SUBSTITUTED-7-OXA-BICYCLO[3.3.0]-OCTANES

[75] Inventor: Roman Kaiser, Uster, Switzerland

[73] Assignee: Givaudan Corporation, Clifton, N.J.

[21] Appl. No.: 7,273

[22] Filed: Jan. 29, 1979

[30] Foreign Application Priority Data

Feb. 9, 1978 [CH] Switzerland ............... 1449/78
Dec. 13, 1978 [CH] Switzerland ............. 12677/78

[51] Int. Cl.³ .................. C07D 307/93; C07D 307/00
[52] U.S. Cl. ........................ 260/346.22; 252/522 R; 426/536
[58] Field of Search ............... 260/346.22, 346.11

[56] References Cited

U.S. PATENT DOCUMENTS 3,812,158 5/1974 Besozzi et al. ............... 260/346.11
3,932,468 1/1976 Kurkey ....................... 260/346.11

OTHER PUBLICATIONS

Kaiser et al., Herbstversammlung des Schw. Chem. Gesellschaft, Bern., Oct. 20, 1978.
Kaiser et al., Helvetica Chimica Acta, vol. 61, No. 1, pp. 373-382 (1978).
Kaiser et al., Helvetica Chemica Acta, vol. 61(1), pp. 383-386 (1978).

Arctander, Perfume and Flavor Materials of Natural Origin (1960) p. 500.

*Primary Examiner*—Henry R. Jiles
*Assistant Examiner*—Bernard Dentz
*Attorney, Agent, or Firm*—Robert F. Tavares; Thomas Cifelli, Jr.

[57] ABSTRACT

The novel odorants and/or flavorants have the formulae:

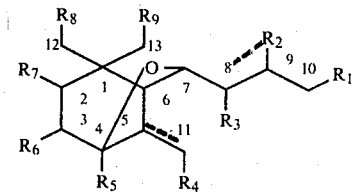

I

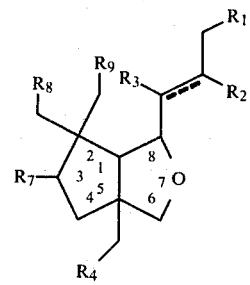

II

12 Claims, No Drawings

MEGASTIGMA-5(11)8-DIEN-4,7-OXIDES AND TETRA-SUBSTITUTED-7-OXA-BICYCLO[3.3.0]-OCTANES

FIELD OF THE INVENTION

This invention relates to odorants and flavorants.

SUMMARY OF THE INVENTION

The invention is concerned with novel odorant and/or flavoring substances, namely compounds of the general formulae:

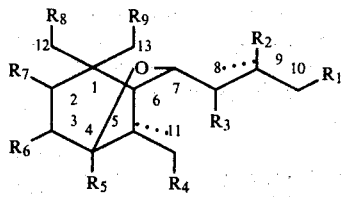

I

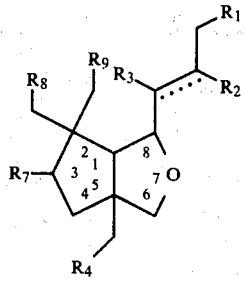

II

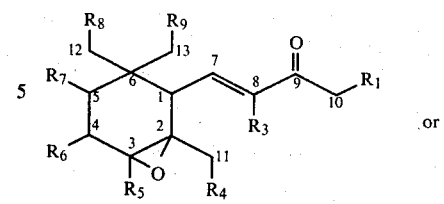

III

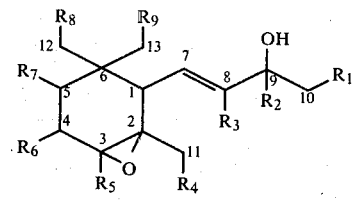

IV wherein $R_1$ and $R_2$ represent a hydrogen atom or a methyl, propyl, vinyl, propenyl or allyl group and $R_3$, $R_4$, $R_5$, $R_6$, $R_7$, $R_8$ and $R_9$ represent a hydrogen atom or a methyl or ethyl group, and the dotted lines represent an optional bond or, when $R_1$ and/or $R_2$ represents a propenyl, vinyl or allyl group, an obligatory bond, and the 5,11-bond in formula I is only saturated when the remainder of the molecule is saturated.

The invention is also concerned with odorant and/or flavoring compositions containing compounds of Formulae I and/or II, a process for the manufacture of the compounds of formulae I and II and the use of compounds of formulae I and II as odorant and/or flavoring substances.

DESCRIPTION OF THE PREFERRED EMBODIMENTS

The preferred compounds are especially the ionone and irone derivatives and the compounds in which $R_2$ and/or $R_3$ represents a methyl group or $R_1$ and/or $R_8$ and/or $R_9$ represents a methyl group.

The invention is also concerned with a process for the manufacture of the novel compounds of formulae I and II. This process comprises treating a compound of the general formula , wherein $R_1$ to $R_9$ have the significance given earlier, with an aluminium sec.alcoholate, the treatment being carried out under reducing conditions when a compound of formula III is used.

The preferred aluminium sec.alcoholates which can be used in the present process are those containing 3–6 carbon atoms.

The preferred aluminium sec.alcoholate is aluminium isopropylate. Further, aluminium sec.-butylate and aluminium sec.amylate are especially suitable.

When a compound of formula III is used as the starting material the treatment with an aluminium sec.alcoholate is carried out under reducing conditions. These conditions can readily be achieved by using an alcoholic solvent such as isopropanol, sec.butanol, sec.amyl alcohol etc.

For the treatment of a compound of formula IV with an aluminium sec.alcoholate there can be used, in principle, the same reagent-solvent system. However, in this case the system need not possess reducing properties, so that aprotic solvents such as toluene, xylene, etc can be used in place of isopropanol etc.

The treatment of a compound of formula III or IV with an aluminium sec.alcoholate is suitably carried out at a temperature between 100° C. and 150° C. The choice of the solvent and the temperature determines the required duration of the treatment. If the treatment of a compound of formula III or IV is carried out, for example, using aluminium isopropylate/isopropanol at 110° C., the time amounts to, for example, 4 to 6 hours. At a temperature of 130° C. the time shortens in this case to 1 to 1.5 hours. If the treatment of a compound of formula IV is carried out using aluminium isopropylate in boiling toluene, the time amounts to 10 to 15 hours, while on the other hand in boiling xylene the time decreases to 5 to 10 hours.

The compounds of formula IV can be prepared in a manner known per se from the compounds of formula III, for example by reduction with sodium borohydride or lithium aluminium hydride.

The products obtained after the aforementioned treatment are conveniently purified by simple distillation. In this manner there is obtained in each case a mixture of a compound of formula I and a compound of formula II in which the proportion of a compound of formula II makes up ca 0.5% to 20%.

The mixtures of the compounds of formulae I and II obtained as the product of the aforementioned process usually need not be separated into the components, since the compounds of formula II (which occur as the byproduct) have similar organoleptic properties to the compounds of formula I. It is therefore economical to use the mixtures.

It is, however, possible to separate the mixtures of the compounds of formulae I and II, for example by means of column chromatography or preparative gas chromatography.

Not only the double bonds in the side chain but also the semicyclic double bonds in the products initially produced can be hydrogenated if desired.

By selective hydrogenation of the (more reactive) double bond in the side chain of compounds of formulae I or II (e.g. using hydrogen in the presence of Pt-IV oxide in ethanol as the solvent) there are obtained the megastigm-5(11)-en-4,7-oxides falling within formula I or the 7-oxa-bicyclo[3.3.0]-octane derivatives falling within formula II.

By exhaustive hydrogenation (e.g. using hydrogen in the presence of a catalyst such as Pt-IV oxide or palladium in a solvent such as ethanol, hexane, ethyl acetate etc) there result ultimately the megastigman-4,7-oxides falling within formula I or on the other hand the 7-oxa-bicyclo[3.3.0]-octane derivatives falling within formula II.

The compounds of formulae I and II are colourless to light yellowish coloured liquids or low melting crystalline substances. They are insoluble in water, but soluble in organic solvents such as, for example, alcohols, ethers, ketones, esters, hydrocarbons and halogenated hydrocarbons.

The compounds of formulae I and II have particular organoleptic properties, on the basis of which they are excellently suited as odorant and/or flavouring substances.

The invention is therefore also concerned with the use of I and II as odorant and/or flavouring substances.

As will be readily evident from Table I hereinafter, the compounds of formulae I and II are characterised by a very broad spectrum of odour or flavour notes.

TABLE 1

Examples of compounds of formulae I and II

| Name | Structure | Odour |
|---|---|---|
| Megastigma-5(11),8-dien-4,7-oxide | 1 | refreshing, fruity, spicy, flowery, camphoraceous, aspects of the top note of geranium oil |
| 2,2,5-Trimethyl-8-[prop-1'-enyl]-7-oxa-bicyclo[3.3.0]-octane | 2 | pleasantly flowery (rose direction), spicy, fruity |
| Megastigm-5(11)-en-4,7-oxide | 3 | camphoraceous, fruity, rosy with spicy aspect |
| Megastigman-4,7-oxide | 4 | fruity, flowery with slight earthy aspect |
| 2-Methyl-megastigma-5(11),8-dien-4,7-oxide | 5 | iris roots, certain aspects of jasmin and black tea, soft and balsamic |
| 2-Methyl-megastigm-5(11)-en-4,7-oxide | 6 | iris roots, sweet, camphoraceous |
| 8-Methyl-megastigma-5(11),8-dien-4,7-oxide | 7 | woody, camphoraceous, fruity |
| 2,2,5-Trimethyl-8-[1'-methyl-prop-1'-enyl]-7-oxa-bicyclo[3.3.0]-octane | 8 | precious wood-like, with fruity-flowery aspect |

TABLE 1-continued
Examples of compounds of formulae I and II

| Name | Structure | Odor |
|---|---|---|
| 8-Methyl-megastigm-5(11)-en-4,7-oxide | 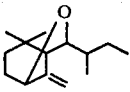 9 | fruity, woody, camphoraceous with slight earthy aspect |
| 9-Methyl-megastigma-5(11),8-dien-4,7-oxide | 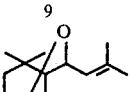 10 | dry woody, cedarous, slightly camphoraceous |
| 2,2,5-Trimethyl-8-[2'-methyl-prop-1'-enyl]-7-oxa-bicyclo-[3.3.0]-octane | 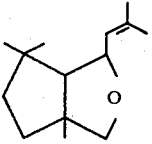 11 | dry wood, camphoraceous, aspects of cedar and costus |
| 9-Methyl-megastigm-5(11)-en-4,7-oxide | 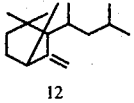 12 | spicy, dry, camphoraceous |
| 9-Ethyl-megastigma-5(11),8-dien-4,7-oxide | 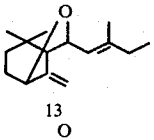 13 | balsamic, woody, dry |
| 10-Methyl-megastigma-5(11),8-dien-4,7-oxide | 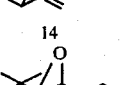 14 | balsamic, green, fruity, camphoraceous |
| 10-Methyl-megastigm-5(11)-en-4,7-oxide | 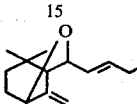 15 | fruity, pleasantly green |
| 10-Allyl-megastigma-5(11),8-dien-4,7-oxide | 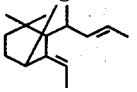 16 | metallic, fruity in the direction of pineapple, slightly flowery |
| 11-Methyl-megastigma-5(11),8-dien-4,7-oxide | 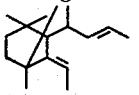 17 | sweet, honey-like, tea-like, rosy |
| 4,11-Dimethyl-megastigma-5(11),8-dien-4,7-oxide | 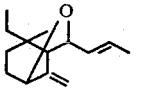 18 | very natural, aromatic, tea-like, aspects of the top notes of geranium and rose oil |
| 12/13-Methyl-megastigma-5(11),8-dien-4,7-oxide | 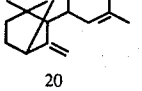 19 | green, grapefruit-like, rosy, aldehydic, camphoraceous |
| 9-Vinyl-megastigma-5(11),8-dien-4,7-oxide | 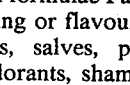 20 | green, balsamic, terpenic |

The compounds of formulae I and II can therefore be used for the perfuming or flavouring of products such as cosmetics (soaps, salves, powders, toothpastes, mouth washes, deodorants, shampoos, lotions, eau de toilette, Eau de Cologne, essences etc), washing agents, detergents, smoking articles, foodstuffs, luxury consumables and drinks, the compounds preferably not being used alone but in the form of compositions which contain other odorant or flavouring substances. Such odorant or flavouring compositions containing a compound of formula I and/or II and their manufacture carried out in a manner known per se (addition of a compound of formula I and/or II to known odorant or flavouring compositions or mixture of a compound of formula I and/or II with natural or synthetic compounds or mixtures suitable as the ingredients of odorant or flavouring compositions) also form objects of the present invention.

On the basis of their valuable olfactory properties the compounds of formulae I and II or mixtures thereof, especially the mixtures having a high content of a compound of formula I, are suitable as odorant and/or flavouring substances, especially in combination with a wide range of natural and synthetic odorant substances or flavouring substances such as, for example:

galbanum oil, mastix oil, vetiver oil, patchouli oil, patchouli leaf oil, sandalwood oil, cedar oil, spruce oil, laurel oil, costus root oil, calamus oil, tree moss absolute, basil oil, mugwort oil, camomile oil, wormwood oil, worm seed oil, celery seed oil, angelica seed oil, star anis oil, thyme oil, rosemary oil, lavander oil, lavandin oil, aspic oil, sage oil, petitgrain oil, neroli oil, bergamotte oil, lemon oil, mandarin oil, orange oil, grapefruit oil, geranium oil, benzoin resinoid, melilotus absolute, jasmin absolute, rose oil, ylang-ylang oil, cananga oil, coriander oil, cassia absolute, narcissus absolute, verbena absolute or oil, violet leaf absolute, tuberose absolute etc, aldehydes such as hydroxycitronellal, cyclamen aldehyde, p-tert.butyl-α-methylhydrocinnamaldehyde, α-hexylcinnamaldehyde, 3,5-dimethyl-cyclohex-3-en-1-yl-carboxaldehyde, citral, citronellal, 2,6-dimethyl-6-hepten-1-al, isovaleraldehyde, trans-2-hexenal, sorbic aldehyde, trans-2-octenal, n-octanal, n-nonanal, trans-2-cis-6-nonadienal, 2,4-decadienal, methylnonyl-acetaldehyde etc, ketones such as α-ionone, β-ionone, acetanisole, 4-(p-hydroxyphenyl)-2-butanone, camphor, menthone, carvone, pulegone etc, acetals and ketals such as phenylacetaldehyde dimethylacetal, phenylacetaldehyde glycerinacetal, 2-methyl-1,3-dioxolan-2-ethyl acetate, capronaldehyde dimethylacetal etc, ethers such as eugenol methyl ether, methyl 1-methylcyclododecyl ether, anethol, estragol etc, phenolic compounds such as eugenol, isoeugenol, creosol etc, alcohols such as butanol, cis-3-hexanol, trans-2-cis-6-nonadienol, cis-6-nonenol, linalool, geraniol, nerol, citronellol, nerolidol, farnesol, benzyl alcohol, phenylethyl alcohol, cinnamic alcohol etc, esters such as methyl dihydrojasmonate, linalyl acetate, geranyl acetate, cedryl acetate, vetiveryl acetate, ethyl isovalerate, ethyl caproate, p-tert.butylcyclohexyl acetate, o-tert.butylcyclohexyl acetate, [4-(4-methyl-3-pentenyl)-3-cyclohexen-1-yl]-methyl acetate, benzyl acetate, benzyl salicylate, styrallyl acetate, ethyl α-methylphenylglycidate, ethyl trans-2-hexenoate, ethyl trans-2-octenoate etc, lactones such as γ-undecalactone, γ-decalactone, γ-nonalactone, δ-decalactone, δ-octalactone, coumarin etc, acids such as lactic acid, butyric acid, α-methylbutyric acid, trans-2-hexenoic acid, trans-2-octenoic acid etc, compounds having a musk-like and amber-like odour such as ethylene brassylate, 4-acetyl-6-tert.butyl-1,1-dimethylindane, 12-oxahexadecanolide, 8α,12-oxido-13,14,15,16-tetranorlabdane etc, sulphur-containing compounds such as p-menthane-8-thiol-3-one, dimethylsulphide and other sulphides and disulphides etc, nitrogen-containing compounds such as methyl anthranilate, indole, isobutylquinoline, various pyrazines etc.

As will be evident from Examples 18 to 32 hereinafter, extremely interesting effects can be achieved with the compounds (megastigmane derivatives) of formula I, which usually are accompanied by ca 0.5% to 20% of the corresponding compounds (7-oxa-bicyclo[3.3.0]-octane derivatives) of formula II, or with the latter compounds.

In addition to producing these original effects in odorant compositions (e.g. compositions of the chypre, cologne, tobacco, wood or rose type or compositions having a generally flowery direction) it is also possible to produce novel perfume complexes with the compounds provided by the present invention. Thus, for example, a 1:1 mixture of geraniol and megastigma-5(11),8-dien-4,7-oxide 1 has an intensive and very diffuse odour which is reminiscent of rhodinol and typical top notes of rose oil and geranium oil. Therefore, this complex is especially suitable for the manufacture of synthetic rose and geranium oils.

Further, megastigma-5(11),8-dien-4,7-oxide 1 is capable of upgrading complexes from linalool/geraniol and citral tremendously by arousing the impression that such valuable natural products as rose oil and lemon oil have been employed in the formulation.

Also, for example, 2-methyl-megastigma-5(11),8-dien-4,7-oxide 5 is capable of binding together in an almost ideal manner the individual elements of a mixture of bergamotte oil, sandalwood oil and methyl dihydrojasmonate and to make the final complex appear very refined, so that it is predestined for use in luxury perfumery.

8-Methyl-megastigma-5(11),8-dien-4,7-oxide 7 is, on the other hand, advantageously used for the rounding-off and intensification of woody complexes which can be composed, for example, of sandalwood oil, patchouli oil, vetiver oil and cedryl acetate.

The concentration of the compounds of formulae I and II can vary within wide limits depending on the purpose of use, for example between about 0.01 wt.% in the case of detergents and about 15 wt.% in the case of alcoholic solutions. In perfume bases or concentrates the concentrations can, of course, also be higher. The perfume bases can be used in the usual manner for the perfuming of Eau de Cologne, eau de toilette, lotions, creams, shampoos, soaps, detergents etc.

As flavouring substances, the compounds of formulae I and II can be used for the production or improvement, intensification, enhancement or modification of fruit or berry flavour in foodstuffs (yoghurt, sweet goods etc), in luxury consumables (tea etc), drinks (lemonades etc) and tobacco.

The pronounced flavour qualities of the compounds of formulae I and II enable them to be used in low concentrations. A suitable range is, for example, 0.1 ppm-100 ppm, preferably 1 ppm-20 ppm, in the finished product (i.e. the flavoured foodstuff, luxury consumable or drink).

In the flavouring of, for example, tobacco the concentration can, however, also be higher and can extend over a wider range; for example, a range of 1 ppm-1000 ppm, preferably 50 ppm-700 ppm.

In Table II hereinafter there are compiled some effects which can be achieved with the compounds of formula I.

TABLE II

| Compound | Flavour | Dosage | Effect |
| --- | --- | --- | --- |
| 1, 2, 17, 18 | Raspberry Tea | ppm in the finished product: 0.1–30 ppm especially 0.5–4 ppm | Greater naturalness of the fruit character, full flavour of the ripe fruit; or typical tea flavour in that woody, herb-fresh and in part also flowery notes appear intensified |
| 19 | Citrus esp. grapefruit | ppm in the finished product: 0.1–100 ppm especially 1–20 ppm | Very natural fruit character, improved top note |
| 16 | Pineapple | ppm in the finished product: 0.1–100 ppm especially 1–20 ppm | Character of the fresh fruit is underlined, rounding-off effect |
| 1, 2, 5, 17, 18 | Tobacco | ppm in the tobacco: 1–1000 ppm especially 50–700 ppm | Upon smoking a pleasant cooling effect, signifi cantly more pleasant and milder flavour |

The compounds provided by the present invention can be mixed with the ingredients used for flavouring compositions or added to such flavourants in the usual manner. Among the flavourants contemplated in accordance with the present invention there are to be understood flavouring compositions which can be diluted or dispersed in edible materials in a manner known per se. The flavouring compositions provided by this invention can be converted according to methods known per se into the usual forms of use, such as solutions, pastes or powders. The present flavouring compositions can be spray-dried, vacuum-dried or lyophilised.

For the production of such usual forms of use there come into consideration, for example, the following carrier materials, thickening agents, flavour-improves, spices, auxiliary ingredients etc:

Gum arabic, tragacanth, salts or brewer's yeast, alginates, carrageen or similar absorbants; maltol, spice oleoresins, smoke flavours; cloves, sodium citrate; monosodium glutamate, disodium inosine-5'-monophosphate (IMP), disodium guanosine-5-phosphate (GMP); or special flavouring substances, water, ethanol, propyleneglycol, glycerine.

The following Examples illustrate the process provided by the present invention:

EXAMPLE 1

Magastigma-5(11),8-dien-4,7-oxide 1 and 2,2,5-trimethyl-8-[prop-1'-enyl]-7-oxabicyclo[3.3.0]-octane 2

(a) A solution of 3.80 g (0.1 mol) of sodium borohydride in 135 ml of ethanol was allowed to drop into a solution of 63.0 g (0.30 mol) of α-ionone epoxide [P. Karrer, H. Sturzinger, Helv. Chim. Acta 29, 1829, (1946)] in 250 ml of ethanol over a period of 20 minutes with slight cooling in such a manner than a temperature of 15° C. was not exceeded. Subsequently, the mixture was stirred at room temperature for a further 20 minutes and diluted with 1 liter of ether. The ether phase was washed neutral, dried with sodium sulphate and concentrated. There were obtained 58 g of crude α-ionol epoxide, of which 56 g were used in the next step.

56.0 g (~0.26 mol) of α-ionol epoxide were dissolved together with 26.5 g (0.13 mol) of aluminium isopropylate in 170 ml of isopropanol, the vessel was placed in an oil bath at 160° C. and nine-tenths of the isopropanol used were distilled off over a 20 cm Vigreux column in such a manner that the temperature of the mixture rose to 130° C. The residual viscous mass was subsequently stirred for 1.5 hours at an oil bath temperature of 145° C. (≙a temperature of the mixture of 130°–135° C.), then cautiously treated with the distilled-off 150 ml of isopropanol, the resulting mixture was cooled down and extracted with ether. The ether phase was washed three times with dilute hydrochloric acid solution and subsequently with water until neutral, dried and concentrated. Distillation of the crude product (48 g) over a 20 cm Widmer column gave 14.3 g (≙28%) of olfactorily good product of boiling point 51°–56° C./0.1 mmHg which contained 90% 1 and 2 in the ratio of 10:1.

(b) 31.2 g (0.15 mol) of α-ionone epoxide were dissolved together with 15.3 g (0.075 mol) of aluminium isopropylate in 90 ml of isopropanol and the solution was subjected to the procedure described under (a). Distillation of the resulting crude product (27 g) gave 8.7 g (≙30.2%) of olfactorily good product which contained above 90% 1 and 2 in the ratio of 10:1. 3.5 g of the 10:1 mixture were separated by means of preparative gas chromatography (GC).

Spectral data

1 IR: 1680, 1222, 1154, 1078, 1054, 1020, 982, 962, 940, 894 cm$^{-1}$

NMR: 0.94+1.02 (each s, each 3 H); 1.67 (d, J~6 Hz, CH$_3$-C(9)); 1.92 (s, 1H-C(6)); 4.36 (d, J~4 Hz, 1H-C(4)); 4.50 (d, J~7 Hz, 1H-C(7)); 4.76+4.97 (each s, each 1H-C(11)); 5.37 (dxd, J (8.9)~15 Hz, J (7.8)~7 Hz read off after w2→1.67 ppm, 1H-C(8)); 5.67 (dxq, J (8.9)~15 Hz, J (9.10)~6 Hz, 1H-C(9)); δ ppm MS: 192 (M+, 9), 177 (15), 163 (8), 159 (10), 122 (74), 107 (100), 93 (42), 91 (25), 79 (30), 41 (19)

2 IR: 1680, 1082, 1055, 978, 966 cm$^{-1}$

NMR: 1.00 (2s, converging 6H); 1.28 (s, CH$_3$-C(5)); 1.72 (d, J~5.5 Hz

CH$_3$); 3.38+3.68 (each d, J gem. ~8.5 Hz, 2H-C(6)); 4.04 (dxd, J each~Hz, 1H-C(8)); 5.56 (dxd, J$_1$~15 Hz, J$_2$~7 Hz,

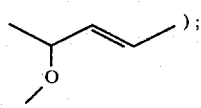

5.80 (dxq, J$_1$~15 Hz, J$_2$~5.5 Hz

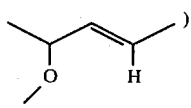

δ ppm

MS: 194 (M+, 17), 179 (21), 125 (100), 109 (66), 95 (22), 81 (33), 69 (43), 67 (42), 55 (34), 41 (50), and further typical fragments at m/e 82 (28), 68 (33).

EXAMPLE 2

Megastigm-5(11)-en-4,7-oxide 3 and 2,2,5-trimethyl-8-propyl-7-oxa-bicyclo[3.3.0]-octane 3a 1.0 g (5.2 mmol) of 1 (+2) were dissolved in 10 ml of ethanol and hydrogenated in the presence of 10 mg of Pt-IV oxide until 140 ml of hydrogen had been taken up. Bulb-tube distillation of the crude product obtained after working-up gave 0.87 g of approximately 90% product 3 and 2,2,5-trimethyl-8-propyl-7-oxa-bicyclo[3.3.0]-octane 3a in the ratio 10:1. For characterisation, a sample of 3 was re-purified by means of preparative GC.

IR: 1685, 1155, 1065, 1058, 972, 968, 890 cm$^{-1}$

NMR: 0.96 (2s, converging, 6H); 0.94 (t, poorly resolved, CH$_3$-C(9)); 4.10 (m, 1H-C(4)); 4.25 (m, 1H-C(7)); 4.72+4.91 (each s, each 1H-C(11)) δ ppm MS: 194 (M+, 4) 179 (23), 151 (46), 135 (17), 122 (37), 107 (77), 95 (100), 81 (81), 69 (39), 55 (35), 41 (56) and further typical fragments at m/e 109 (39), 93 (42), 91 (36), 79 (41), 67 (35).

EXAMPLE 3

Megastigman-4,7-oxide 4 and 2,2,5-trimethyl-8-propyl-7-oxa-bicyclo[3.3.0]-octane 4a 3.7 g (19 mmol) of 1 (+2) were dissolved in 25 ml of ethanol and hydrogenated in the presence of 60 mg of Pt-IV oxide until 940 ml of hydrogen had been taken up. Bulb-tube distillation of the crude product obtained after working-up gave 3.35 g of above 90% 4 and 2,2,5-trimethyl-8-propyl-7-oxa-bicyclo[3.3.0]-octane 4a in the ratio 10:1. A sample of 4 purified by means of preparative GC showed the following spectral data.

IR: 1238, 1163, 1142, 1072, 1042, 982, 969, 954 cm$^{-1}$

NMR: 0.91+1.10 (each s, each 3H); 0.94 (t, J~6.5 Hz, CH$_3$-C(9)); 2.28 (2m, 1H-C(5) and 1H-C(6)); 4.00 (2m, overlapped, 1H-C(4) and 1H-C(7)) δ ppm MS: 196 (M+, 1), 153 (100), 135 (24), 109 (50), 97 (19), 95 (51), 81 (15), 69 (27), 55 (22), 43 (12), 41 (25).

EXAMPLE 4

2-Methylmegastigma-5(11), 8-dien-4,7-oxide 5 and 2,2,3,5-tetramethyl-8-[propyl-1'-enyl]-7-oxa-bicyclo[3.3.0]-octane 5a 198 g (1.1 mol) of 40% peracetic acid were added dropwise while stirring over a period of 40 minutes to a mixture, cooled to 0° C., of 206.0 g (1 mol) of α-irone and 198 g of anhydrous sodium acetate in 1 liter of methylene chloride in such a manner that the temperature lay between 10° C. and 15° C. Subsequently, the external cooling source was removed and the mixture was stirred for 4 hours. In the course of the first hour the temperature of the mixture rose to 30° C. and thereafter fell back slowly to room temperature. The sodium acetate was removed by filtration, the clear solution was washed three times with water, three times with sodium sulphite solution, three times with sodium bicarbonate solution and once more with water, dried with sodium sulphate and concentrated. There were obtained 215 g of crude product which contained above 92% α-irone epoxide in accordance with GC. By distillation over a 30 cm Widmer column there were obtained 190 g of α-irone epoxide (≙86%) of boiling point 100°-101° C./0.06 mmHg.

55.5 g (0.25 mol) of α-irone epoxide were dissolved together with 38.4 g (0.19 mol) of aluminum isopropylate in 180 ml of isopropanol and subjected to the procedure described in Example 1. Distillation of the crude product (54 g) over a 10 cm Widmer column gave 13.2 g (≙25.6%) of olfactorily good product of boiling point 60°-63° C./0.2 mmHg which consisted to above 90% of 5 and 2,2,3,5-tetramethyl-8-[prop-1'-enyl]-7-oxa-bicyclo[3.3.0]-octane 5a in the ratio ~20:1.

Spectral data of 5

IR: 1680, 1040, 1030, 980, 968, 910, 890 cm$^{-1}$

NMR: 0.78+1.02 (each s, each 3H); 1.00 (d, J~6.5 Hz, CH$_3$-C(2)); 1.67 (d, J~6 Hz, CH$_3$-C(9)); 1.92 (s, 1H-C(6)); 4.34 (d, J~4 Hz, 1H-C(4): 4.50 (d, J~7 Hz, 1H-C(7)); 4.76+4.96 (each s, each 1H-C(11)); 5.26-5.86 (m, 1H-C(8) and 1H-C(9), signal analysis: compare NMR of 1)

MS: 206 (M+, 1) 136 (50), 121 (100), 109 (36), 107 (69), 93 (45), 79 (39), 77 (27), 67 (28), 55 (26), 41 (45).

EXAMPLE 5

2-Methylmegastigm-5(11)-en-4,7-oxide 6 and 2,2,3,5-tetramethyl-8-propyl-7-oxa-bicyclo[3.3.0]-octane 6a 2.06 g (10 mmol) of 5 were dissolved in 20 ml of ethanol and hydrogenated in the presence of 20 mg of Pt-IV oxide until 270 ml of hydrogen had been taken up. Bulb-tube distillation of the crude product obtained after working-up gave 1.75 g of approximately 88% 6 and 2,2,3,5-tetramethyl-8-propyl-7-oxa-bicyclo[3.3.0]-octane 6a in the ratio ~20:1. For characterisation, a sample of 6a was re-purified by means of preparative GC.

IR: 1690, 1078, 1062, 1053, 1032, 890 cm$^{-1}$

NMR: 0.78+0.97 (each s, each 3H); 0.77 (d, J~6.5 Hz, CH$_3$-C(2)); ~0.9 (t, poorly resolved, CH$_3$-C(9)); 1.85 (s, 1H-C(6)); 4.05 (m, 1H-C(4)); 4.26 (m, 1H-C(7)); 4.72+4.90 (each s, each 1H-C(11)) δ ppm MS: 208 (M+, 16), 193 (60), 165 (100), 149 (51), 136 (46), 121 (87), 109 (76), 95 (89), 81 (53), 69 (34), 55 (39), 41 (67) and further typical fragments at m/e 167 (76), 137 (40), 123 (58), 107 (49).

EXAMPLE 6

8-Methylmegastigma-5(11),8-dien-4,7-oxide 7 and 2,2,5-trimethyl-8-[1'-methylprop-1'-enyl]-7-oxabicyclo[3.3.0]-octane 8

206.0 g (1 mol) of isomethyl-α-ionone were epoxidised in a manner analogous to the epoxidation of α-irone described in Example 4. Distillation of the crude product over a 20 cm Widmer column gave 194 g (above 88%) of above 94% pure isomethyl-α-ionone epoxide of boiling point 94°-95° C./0.06 mmHg.

80.0 g (0.36 mol) of isomethyl-α-ionone epoxide were dissolved with 36.8 g (0.18 mol) of aluminum isopropylate in 240 ml of isopropanol and subjected to the procedure described in Example 1. Distillation of the crude product (77 g) over a 15 cm Widmer column gave 28.1 g (≙38%) of olfactorily good product of boiling point 68°-72° C./0.09 mmHg which contained above 80% 7 and 8 in the ratio of approximately 9:1. 2.5 g of the 9:1 mixture were separated by means of preparative GC.

Spectral data of 7 and 8

7 IR: 1680, 1060, 1055, 990, 968, 890 cm⁻¹

NMR: 0.98+1.06 (each s, each 3H); 1.56 (s, CH₃-C(8)); 1.60 (d, J~6.5 Hz, CH₃-C(9)); 1.94 (s, 1H-C(6)); 4.4-4.5 (1H-C(4) and 1H-C(7), overlapped; 4.68 and 4.94 (each s, each 1H-C(11)); 5.44 (m, 1H-C(9)).

MS: 206 (M+, 2), 122 (57), 107 (100), 93 (41), 91 (24), 79 (38), 77 (17), 67 (13), 55 (21), 41 (29), 39 (14).

8 IR: 1680, 1082, 1060, 965, 827, 807 cm⁻¹

NMR: 0.97 (2s converging, 6H); 1.28 (s, CH₃C(5)); 1.60 (d with fine resolution, 1.66 (s,

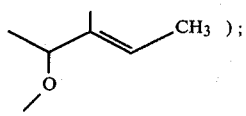

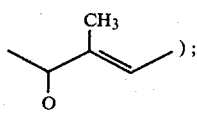

3.36+3.68 (each d, J mix.~8.5 Hz, 2H-C(6)); 4.02 (d, J~7 Hz, 1H-C(8)); 5.50 (m,

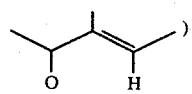

MS: 208 (M+, 96), 193 (100), 139 (93), 109 (24), 95 (24), 82 (36), 69 (55), 68 (40), 55 (38), 41 (44).

EXAMPLE 7

8-Methylmegastigm-5(11)-en-4,7-oxide 9 and 2,2,5-trimethyl-8-[1'-methylpropyl]-7-oxa-bicyclo[3.3.0]-octane 9a 7.0 g (0.034 mol) of 7 (+8) were dissolved in 70 ml of methanol and hydrogenated in the presence of 70 mg of Pt-IV oxide until 870 ml of hydrogen had been taken up. Bulb-tube distillation of the crude product obtained after working-up gave 8.6 g of approximately 87% 9 and 2,2,5-trimethyl-8-[1'-methylpropyl]-7-oxa-bicyclo[3.3.0]-octane 9a in the ratio ~9:1. A sample of 9 was re-purified by means of preparative GC.

IR: 1685, 1059, 968, 890 cm⁻¹

NMR: 0.97 (2 s converging, 6H), 0.75-0.95 (t, CH₃-C(9) and d CH₃-C(8), overlapping); 2.00 (s, 1H-C(6)); 3.80 and 4.29 (each m, 1H-C(4), 1H-C(7)); 4.71+4.91 (each s, each 1H-C(11)) δ ppm MS: 208 (M+, 1), 151 (10), 138 (14), 123 (54), 109 (19), 107 (35), 95 (100), 81 (36), 69 (18), 55 (20), 41 (45).

EXAMPLE 8

9-Methylmegastigma-5(11),8-dien-4,7-oxide 10 and 2,2,5-trimethyl-8-[2'-methylprop-1'-enyl]-7-oxabicyclo[3.3.0]-octane 11.

A solution of 50.0 g (0.26 mol) of α-ionone in 150 ml of ether were allowed to drop over a period of 20 minutes into a Grignard solution, which was cooled to 0° C. and which had been prepared from 7.5 g (0.31 mol) of magnesium shavings in 75 ml of ether and 46.9 (0.33 mol) of methyl iodide in 180 ml of ether, in such a manner that the temperature lay between 10° C. and 20° C. Subsequently, the mixture was stirred at the reflux temperature of the ether for a further 1 hour, cooled down to 0° C. and then cautiously treated with concentrated ammonium chloride solution and an additional 500 ml of ether. The ether phase was washed with water until neutral, dried and concentrated. There were obtained 60.0 g of crude product which contained above 95% 9-methyl-α-ionol (GC) and which was accordingly further processed directly in this form. In a manner analogous to the epoxidation of α-irone (Example 4), from 58.1 g (~0.26 mol) of 9-methyl-α-ionol there was obtained 68.0 g of crude 9-methyl-α-ionol epoxide.

66.9 g (0.25 mol) of crude 9-methyl-α-ionol epoxide were dissolved together with 26.5 g (0.13 mol) of aluminium isopropylate in 200 ml of isopropanol and subjected to the procedure described in Example 1. Distillation of the crude product (64.0 g) over a 20 cm Widmer column gave 20.7 g ( 39%) of olfactorily good product of boiling point 67°-71° C./0.08 mmHg which contained above 90% of 10 and 11 in the ratio of 8:1. 2.2 g of the 8:1 mixture were separated by means of preparative GC.

Spectral data of 10 and 11

10 IR: 1680, 1053, 1019, 982, 961, 889 cm⁻¹

NMR: 0.97+1.03 (each s, each 3H); 1.72 (2 converging s, 2 CH₃-C(9)); 1.88 (s, 1H-C(6)); 4.36 (d, J~4 Hz, 1H-C(4)); 4.82 (d, J~8 Hz, 1H-C(7)); 4.76+4.94 (each s, each 1H-C(11); 5.12 (d with fine resolution J~8 Hz, 1H-C(8)) δ ppm MS: 206 (M+, 9), 191 (11), 150 (11), 122 (65), 107 (100), 93 (40), 91 (27), 85 (21), 79 (24), 55 (13), 41 (25).

11 IR: 1680, 1053, 1009, 978, 961 cm⁻¹

NMR: 0.90+0.98 (each s, each 3H); 1.23 (s, CH₃-C(5)); 1.73+1.74 (each s,

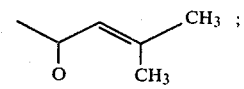

3.31+3.65 (each d, J mix.~8 Hz, 2H-C(6)); 4.20 (dxd, J each 8 Hz, 1H-C(8)); 5.20 (d with fine resolution J~8 Hz,

δ ppm

MS: 208 (M+, 114), 193 (100), 139 (22), 109 (47), 95 (14), 85 (19), 82 (23), 69 (49), 68 (27), 55 (21), 41 (28).

EXAMPLE 9

9-Methylmegastigm-5(11)-en-4,7-oxide 12 and 2,2,5-trimethyl-8-isobutyl-7-oxa-bicyclo[3.3.0]-octane 12a 2.06 g (10 mmol) of 10 (+11) were dissolved in 20 ml of ethanol and hydrogenated in the presence of 20 mg of Pt-IV oxide until 260 ml of hydrogen had been taken up. Bulb-tube distillation of the crude product obtained after working-up gave 1.90 g of approximately 89% 12 and 2,2,5-trimethyl-8-isobutyl-7-oxa-bicyclo[3.3.0]- octane 12a in the ratio ~8:1. A sample of 12 was re-purified by means of preparative GC.

IR: 1680, 1062, 1057, 981, 967, 889 cm⁻¹

NMR: ~0.95 (d, J~6 Hz, 2 CH₃-C(9)); 1.00 (2s, converging, 6H); 1.86 (s, 1H-C(6)); 4.20+4.30 (each m, 1H-C(4)); 1H-C(7); 4.77+4.97 (each s, each 1H-C(11)) δ ppm MS: 208 (M+, 11), 193 (45), 165 (40), 151 (54), 122 (49), 107 (66), 95 (100), 81 (62), 69 (57), 55 (37), 41 (71) and further typical fragments at m/e 123 (43), 109 (54), 93 (42), 79 (36).

EXAMPLE 10

9-Ethylmegastigma-5(11),8-dien-4,7-oxide 13 and 2,2,5-trimethyl-8-[2'-methyl-but-1'-enyl]-7-oxa-bicyclo[3.3.0]-octane 13a In a manner analogous to that described in Example 8 for the preparation of 9-methyl-α-ionol, from 50.0 g (0.26 mol) of α-ionone and 0.31 mol of ethylmagnesium bromide in ether there were obtained 59.0 g of crude product which contained above 90% (GC) 9-ethyl-α-ionol and which was further processed directly in this form. The epoxidation of 55.7 g (~0.25 mol) of crude 9-ethyl-α-ionol carried out in a manner analogous to that described in Example 4 gave 57.8 g 90% 9-ethyl-α-ionol epoxide, of which 56.8 g were dissolved with 24.5 g (0.12 mol) of aluminum isopropylate in 100 ml of isopropanol. By following the procedure described in Example 1 there were obtained 54.0 g of a crude product from which there were obtained by distillation over a 20 cm Widmer column 12.2 g (~23%) of olfactorily good product of boiling point 73°-76° C./0.05 mmHg which contained above 90% 13 and the corresponding 7-oxa-bicyclo[3.3.0]-octane derivative, the 2,2,5-trimethyl-8-[2-methyl-but-1enyl]-7-oxa-bicyclo[3.3.0]-octane 13a, in the ratio of 10:1.

Spectral data of 13

IR: 1675, 1052, 1028, 982, 962, 888 cm⁻¹

NMR: 0.94+1.01 (each s, each 3H); 1.0 (t, CH₃-C(10)); 1.72 (s, CH₃-C(9)); 1.86 (s, 1H-C(6)); 4.36 (d, J~4 Hz, 1H-C(4)); 4.82 (d, J~8 Hz, 1H-C(7)); 4.76+4.94 (each s, each 1H-C(11); 5.13 (d with fine resolution, J~8 Hz, 1H-C(8)); δ ppm MS: 220, (M+, 8), 137 (122 (77), 107 (100), 99 (35), 93 (36), 79 (18), 69 (7), 55 (10), 41 (17).

EXAMPLE 11

10-Methylmegastigma-5(11),8-dien-4,7-oxide 14 and 2,2,5-trimethyl-8-[but-1-enyl]-7-oxa-bicyclo[3.3.0]-octane 14a 12.0 g (0.054 mol) of n-methyl-α-ionone epoxide were dissolved together with 5.5 g (0.027 mol) of aluminium isopropylate in 35 ml of isopropanol and subjected to the procedure described in Example 1. Distillation of the crude product (11.5 g) over a 10 cm Widmer column gave 2.8 g (=25%) of olfactorily good product of boiling point 60°-61° C./0.04 mmHg which contained 90% 14 and 2,2,5-trimethyl-8-[but-1-enyl]-7-oxa-bicyclo[3.3.0]-octane 14a in the ratio of 10:1. A sample of 14 was re-purified by means of preparative GC.

Spectral data of 14

IR: 1685, 1225, 1155, 1053, 988, 970, 960, 890 cm⁻¹

NMR: 0.96+1.02 (each s, each 3H); 0.98 (t, J~7 Hz, CH₃—C(10)); 1.92 (s, 1H—C(6)); 4.36 (d, J~4 Hz, 1H—C(4)); 4.51 (d, J~7 Hz, 1H—C(7)); 4.76+4.96 (each s, each 1H-C(11)); 5.2-5.8 (m, 1H—C(8) and 1H—C(9), signal analysis:compare NMR of 1)

MS: 206 (M+, 1), 122 (56), 107 (100), 93 (40), 91 (26), 81 (22), 79 (41), 77 (20), 67 (20), 55 (27), 41 (38).

EXAMPLE 12

10-Methylmegastigm-5(11)-en-4,7-oxide 15 and 2,2,5-trimethyl-8-butyl-7-oxa-bicyclo[3.3.0]-octane 15a 1.03 g (5 mmol) of 14 were dissolved in 10 ml of ethanol and hydrogenated in the presence of 10 mg of Pt-IV oxide until 130 ml of hydrogen had been taken up. Bulb-tube distillation of the crude product obtained after working-up gave 0.80 g of approximately 85% product containing 15 and 2,2,5-trimethyl-8-butyl-7-oxa-bicyclo[3.3.0]-octane 15a in the ratio of 10:1. A sample of 15 purified by means of preparative GC showed the following spectral data:

IR: 1685, 1155, 1058, 967, 890 cm⁻¹

NMR: 0.92 (2s, converging, 6H); 1.83 (s, 1H—C(6)); 4.02+4.29 (each m, 1H—C(4) and 1H—C(7)); 4.72+4.92 (each s, each 1H—C(11)) δppm MS: 208 (M+, 18), 193 (82), 165 (51), 151 (84), 122 (60), 109 (53), 107 (80), 95 (100), 81 (58), 69 (29), 41 (62) and further typical fragments at m/e 164 (38), 123 (51), 93 (38), 79 (32), 67 (27).

EXAMPLE 13

10-Allylmegastigma-5(11),8-dien-4,7-oxide 16 and 2,2,5-trimethyl-8-[hexa-1',5=-dienyl]-7-oxa-bicyclo[3.3.0]-octane 16a.

30.6 g (0.12 mol) of n-allyl-α-ionone epoxide, prepared from commercial n-allyl-α-ionone, were dissolved together with 12.6 g (0.06 mol) of aluminium isopropylate in 100 ml of isopropanol and subjected to the procedure described in Example 1. Distillation of the crude product (28.2 g) over a 10 cm Widmer column gave 6.3 g (≙27%) of olfactorily good product of boiling point 78°-80° C./0.04 mmHg which contained above 90% 16 and 2,2,5-trimethyl-8-[hexa-1',5'-dienyl]-7-oxa-bicyclo[3.3.0]-octane 16a in the ratio of 10:1. A sample of 16 purified by means of preparative GC showed the following spectral data.

IR: 1685, 1645, 1225, 1151, 1052, 990, 980, 960, 910, 890 cm⁻¹

NMR: 0.90+0.97 (each s, each 3H); 1.87 (s, 1H—C(6)); 2.08 (m,

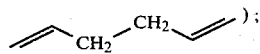

4.33 (d, J~4 Hz, 1H—C(4)); 4.50 (d, J~7 Hz, 1H—C(7)); 4.72+4.92 (each s, each 1H—C(11)); 4.8–5.8 (m, 5H) δppm MS: 232 (M+, 1), 122 (56), 107 (100), 93 (54), 91 (38), 81 (19), 79 (42), 77 (25), 67 (15), 55 (16), 41 (36).

EXAMPLE 14

11-Methylmegastigma-5(11),8-dien-4,7-oxide 17 and the corresponding 7-oxa-bicyclooctane 17a The acid catalysed reaction of 3-ethyl-7-methyl-oct-1-yn-6-en-3-ol with isopropenyl methyl ether and subsequent base-catalysed isomerisation of the resulting β-ketoallene (G. Saucy, R. Marbet, Helv. 50, 1158, 1967) gave a good yield of 6-ethyl-10-methyl-undeca-3,5,9-trien-2-one which was cyclised with 85% phosphoric acid in a known manner [H. Rouve, M. Stoll, Helv. 30, 2216 (1947)]. The resulting product contained 90% 11-methyl-α-ionone and 11-methyl-γ-ionone (two isomers) in the ratio of 7:3. In a manner analogous to the epoxidation of α-ionone (Example 4), from 13.4 g (0.065 mol) of 11-methyl-α-ionone there were obtained 13.9 g of crude 11-methyl-α-ionone epoxide of which 13.4 g (~0.06 mol) were dissolved together with 6.1 g (0.03 mol) of aluminium isopropylate in 30 ml of isopropanol. By following the procedure described in Example 1 there were obtained 13.7 g of a crude product. From this crude product there were obtained by distillation over a 5 cm Widmer column 2.10 g (17%) of olfactorily good product of boiling point 73°-75° C./0.05 mmHg and which contained above 85% 17 and the corresponding 7-oxa-bicyclooctane 17a. A sample purified by means of preparative GC showed the following spectral data:

IR: 1680, 1152, 1050, 877, 962 cm$^{-1}$

NMR: 0.92+1.00 (each s, each 3H); 1.65 (2 d, overlapped, CH$_3$—C(9) and CH$_3$—C(11)); 4.28 (d, J~4 Hz, 1H—C(4)); 4.47 (d, J~7 Hz, 1H—C(7)); 5.1-5.9 (m, 1H—C(8), 1H—C(9) and 1H—C(11)) δppm MS: 206 (M$^+$, 8), 136 (90), 121 (100), 109 (41), 107 (91), 93 (82), 91 (47), 79 (48), 67 (41), 55 (38), 41 (60).

EXAMPLE 15

4,11-Dimethylmegastigma-5(11),8-dien-4,7-oxide 18 and the corresponding 7-oxa-bicyclooctane 18a The cyclisation of 6-ethyl-7,10-dimethyl-undeca-3,5,9-trien-2-one (prepared in a manner analogous to that described in Example 14) with 85% phosphoric acid gave a product which contained 90%, 3,11-dimethyl-α-ionone and 3,11-dimethyl-γ-ionone (two isomers) in the approximate ratio of 7:3. In a manner analogous to the epoxidation of α-irone (Example 4), from 50.0 g (0.23 mol) of 3,11-dimethyl-α-ionone there were obtained 54 g of crude 3,11-dimethyl-α-ionone epoxide of which 49 g (~0.21 mol) were dissolved together with 21.4 g (0.105 mol) of aluminium isopropylate in 80 ml of isopropanol. By following the procedure described in Example 1 there were obtained 46 g of a crude product. From this crude product there were obtained by distillation over a 10 cm Widmer column 4.4 g (~10%) of olfactorily good product of boiling point 72°-74° C./0.04 mmHg which contained above 70% 18 and the corresponding 7-oxa-bicyclooctane 18a. For characterisation, a sample purified by column chromatography was used.

IR: 1680, 1232, 1162, 1155, 1128, 1092, 1026, 980, 965, 952, 935, 840, 820 cm$^{-1}$

NMR: 0.92+1.04 (each s, each 3H); 1.30 (s, CH$_3$—C(4)); 1.66 (2 d, overlapped, J each ~7 Hz, CH$_3$—C(9) and CH$_3$—C(11)); 2.32 (s, 1H—C(6)); 4.42 (d, J~7 Hz, 1H—C(7)); 5.1-5.8 (m, 1H—C(8), 1H—C(9) and 1H—C(11)) δppm MS: 220 (M$^+$, 29), 177 (97), 149 (57), 135 (87), 121 (89), 109 (100), 107 (78), 91 (48), 81 (32), 55 (30), 43 (81) and further typical fragments at m/e 123 (50), 95 (30), 93 (42), 79 (28), 67 (26), 41 (42)

EXAMPLE 16

12/13-Methylmegastigma-5(11),8-dien-4,7-oxide 19 and corresponding 7-oxa-bicyclooctane 19a The cyclisation of 6,10-dimethyl-dodeca-3,5,9-trien-2-one (prepared in a manner analogous to that described in Example 14) with 85% phosphoric acid gave a product which contained above 90% 12/13-methyl-α-ionone and 12/13-methyl-β-ionone in the approximate ratio of 9:1. In a manner analogous to the epoxidation of α-irone (Example 4), from 52.7 g (0.256 mol) of 12/13-methyl-α-ionone there were obtained 49.0 g (85%) 12/13-methyl-α-ionone epoxide of boiling point 109°-111° C./0.3 mmHg of which 19.2 g (0.086 mol) were dissolved together with 8.8 g (0.043 mol) of aluminium isopropylate in 50 ml of isopropanol. By following the procedure described in Example 1 there were obtained 17.8 g of a crude product. From this crude product there were obtained by distillation over a 10 cm Widmer column 4.0 g ($\triangleq$17.7%) of olfactorily good product of boiling point 70°-73° C./0.3 mmHg which contained above 85% 19 besides the corresponding 7-oxa-bicyclooctane 19a. A sample purified by means of preparative GC showed the following spectral data:

IR: 1685, 1220, 1155, 1056, 990, 963, 944, 890 cm$^{-1}$

NMR: ~0.90 (t, CH$_3$—C (12/13)); 0.92 (s, 3H); 1.68 (d, J~6 Hz, CH$_3$—C(9)); 2.02 (s, 1H—C(6)); 4.32 (d, J~4 Hz, 1H—C(4)); 4.50 (d, J~7 Hz, 1H—C(7)); 4.80+4.97 (each s, each 1H—C(11)); 5.2-5.8 (m, 1H—C(8) and 1H—C(9)) δppm MS: 206 (M$^+$, 5), 177 (32), 136 (59), 121 (50), 107 (100), 93 (50), 91 (40), 79 (49), 67 (16), 55 (25), 41 (41).

EXAMPLE 17

9-Vinylmegastigma-5(11),8-dien-4,7-oxide 20 and corresponding 7-oxa-bicyclooctane 20c A solution of 50 g (0.26 mol) of α-ionone in 150 ml of tetrahydrofuran was allowed to drop over a period of 20 minutes into a Grignard solution, which was cooled to 0° C. and which had been prepared from 9.72 g (0.4 mol) of magnesium shavings in 75 ml of tetrahydrofuran and 44.9 g (0.42 mol) of vinyl bromide in 180 ml of tetrahydrofuran, in such a manner that the temperature lay between 15° C. and 20° C. Subsequently, the mixture was stirred at room temperature for a further 3 hours and worked-up as described in Example 8. There were obtained 54.5 g of crude product which contained above 92% 9-vinyl-α-ionol according to GC and which was further processed directly in this form. In a manner analogous to the epoxidation of α-irone (Example 4), from 53.2 g (0.242 mol) of 9-vinyl-α-ionol there were obtained 59.0 g of crude 9-vinyl-α-ionol epoxide of which 58.0 g were dissolved together with 26.5 g (0.13 mol) of aluminium isopropylate in 175 ml of isopropanol. By following the procedure described in Example 1 there were obtained 57 g of a crude product. From this crude product there were obtained by distillation over a 20 cm Widmer column 15.0 g ($\triangleq$26%) of olfactorily good product of boiling point 73°-74° C./0.3 mmHg which contained above 85% 20a and 20b in the approximate ratio of 3:2. In addition, there were present small amounts of the corresponding 7-oxa-bicyclooctane 20c.

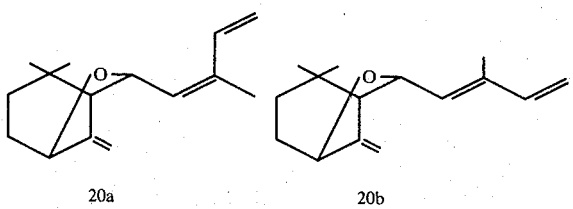

20a      20b

Spectral data of 20a and 20b

20a IR: 1680, 1600, 1052, 990, 980, 960, 905, 890 cm$^{-1}$

NMR: 0.96+1.04 (each s, each 3H); 1.82 (s, CH$_3$C(9)); 1.92 (s, 1H—C(6)); 4.38 (d, J~4 Hz, 1H—C(4)); 5.04 (d, J~7 Hz, 1H—C(7)); 4.80+4.98

(each s, each 1H—C(11); 5.2 (m, 1H—C(8)); 5.1–5.4 (m,

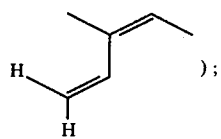

6.72–7.02 (m,

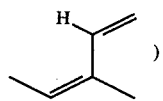

δppm

MS: 218 (M+, 14), 150 (9), 122 (65), 107 (100), 97 (35), 93 (39), 79 (19), 67 (5), 55 (8), 41 (13)

20b IR: 1680, 1605, 1056, 992, 988, 963, 905, 898 cm$^{-1}$

NMR: 0.98+1.04 (each s, each 3H); 1.84 (s, CH$_3$—C(9)); 1.94 (s, 1H—C(6)); 4.40 (d, J~4 Hz, 1H—C (4)); 4.96 (d, J~7 Hz, 1H—C(7)); 4.80+4.98 (each s, each 1H—C(11)); ~5.1 (m, 1H—C(8)); 5.05–5.5 (m,

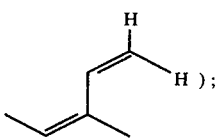

6.2–6.5 (m,

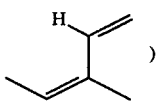

δppm

MS: 218 (M+, 15), 150 (10), 122 (65), 107 (100), 97 (41), 93 (38), 79 (25), 68 (17), 55 (10), 41 (18).

The following Examples illustrate the use of the novel compounds provided by the present invention in odorant and flavouring compositions. In these Examples the reference to a compound of formula I means a mixture of a compound of formula I and a small amount of a compound of formula II prepared according to the process provided by this invention. It will, however, be appreciated that a compound of formula I alone can be used in place of this mixture.

EXAMPLE 18

Perfume complex containing megastigma-5(11),8-dien-4,7-oxide 1

|  | Parts by weight |
|---|---|
| Geraniol extra | 450 |
| 2-Ethyl-3,6,6-trimethyl-2-cyclohexen-1-yl carboxylic acid ethyl ester | 450 |
|  | 900 |

When 100 parts of 1 are added to this complex, then it is rounded-off very pleasantly and becomes rather like a base in the direction of rose. There results a very spicy rose note with pronounced diffusion and fullness. On the other hand, when the complex is modified by mixing only geraniol with 1 in the ratio 1:1, then there is obtained an amazing effect in the direction of rhodinol. There is obtained a rose base having a very intensive top note which is very well suited for rose compositions having a very modern note. Moreover, there is obtained an increase in the tenacity of the geraniol.

EXAMPLE 19

Perfume complex containing megastigma-5(11),8-dien-4,7-oxide 1

|  | Parts by weight |
|---|---|
| Linalool synthetic | 200 |
| Geraniol synthetic | 720 |
| Citral | 50 |
|  | 970 |

When 30 parts of megastigma-5(11),8-dien-4,7-oxide are added to this fresh-flowery complex, then it takes on a pleasant freshness and, with reference to the flower note, is more natural. The impression is now given that natural rose oil and lemon oil have been used together in small amounts in the production of the complex.

EXAMPLE 20

Perfume complex containing 2-methyl-megastigma-5(11) 8-dien-4,7-oxide 5

|  | Parts by weight |
|---|---|
| Bergamotte oil | 200 |
| Sandalwood oil | 200 |
| Methyl dihydrojasmonate | 200 |
|  | 600 |

This complex, which can be used in luxury perfumery, is very much softer, more harmonious and more natural after the addition of 400 parts of 5. The novel 5 binds the sandalwood oil/methyl dihydrojasmonate note almost perfectly. There is obtained a complex which is very refined. When the concentration of 5 is reduced and there is added, for example, only 100 parts thereof, then there is obtained a complex having a quite different direction. The citrus direction alters. While the bergamotte oil dominates in the original base, the complex now tends rather in the direction of lemon oil.

EXAMPLE 21

Perfume complex (wood direction) containing 8-methyl-megastigma-5(11),8-dien-4,7-oxide 7

|  | Parts by weight |
|---|---|
| Sandalwood oil | 340 |
| Patchouli oil | 340 |
| Vetiver oil | 200 |
| Cedryl acetate | 60 |
|  | 940 |

When 60 parts of 7 are added to this "wood complex", then it is altered markedly in the direction of sandalwood. It arouses the impression of freshly cut, young wood. The novel complex is more powerful and more diffuse.

EXAMPLE 22

Perfume base containing megastigma-5(11),8-dien-4,7-oxide 1

|  | Parts by weight |
| --- | --- |
| Propyleneglycol | 190 |
| Phenylethyl alcohol | 400 |
| Geraniol extra | 100 |
| Nerol | 100 |
| Cinnamyl propionate | 70 |
| Cinnamic alcohol | 60 |
| α-Ionone | 20 |
| 4-Acetyl-6-tert.butyl-1,1-dimethyl-indane | 10 |
| Rose oxide (10% in propyleneglycol) | 10 |
| Geranium Bourbon oil (10% in propyleneglycol) | 10 |
|  | 970 |

When 30 parts of 1 are added to this rose base, then it is enhanced, more fruity, the geranium note is underlined impressively and there is now produced a more typical rose note. The weight balance between the geranium oil and the geraniol seems arranged in the novel base so that a very fine rhodinol effect is obtained.

EXAMPLE 23

Perfume composition (tea direction) containing megastigma-5(11),8-dien-4,7-oxide 1

|  | Parts by weight |
| --- | --- |
| Bergamotte oil | 240 |
| Hydroxycitronellal | 120 |
| Methyl dihydrojasmonate | 120 |
| Patchouli leaf oil | 60 |
| Basil oil | 60 |
| Cedryl acetate crystalline | 60 |
| Acetanisole | 40 |
| β-Ionone | 40 |
| 12-Oxa-hexadecanolide | 40 |
| Tree moss absolute (50% in propyleneglycol) | 20 |
| Lemon oil | 20 |
| Acetylated cedar wood oil | 20 |
| Mugwort oil | 20 |
| Camomile oil Roman (10% in propyleneglycol) | 20 |
| Indole (10% in propyleneglycol) | 10 |
| Rhodinol | 10 |
| Thibetolide (ω-pentadecalactone) | 10 |
| Spruce needle balsam absolute | 6 |
| Wormseed oil | 4 |
| Methyleugenol | 60 |
|  | 980 |

When 20 parts of 1 are added to this perfume composition, then a desirable tea effect comes into play. The composition is more flowery, more powerful and more aromatic. The camomile character is underlined markedly. 1 exhibits a very good, harmonising and binding effect in this composition.

EXAMPLE 24

Perfume composition (general flowery direction) containing megastigma-5(11),8-dien-4,7-oxides [1 or 7] or oxa-bicyclo[3.3.0]-octanes [2 or 8]

|  | Parts by weight |
| --- | --- |
| Phenylethyl-phenyl acetate | 150 |
| Benzyl salicylate | 130 |
| Methyl 1-methylcyclododecyl ether | 120 |
| Glyceryl acetate of phenylacetaldehyde | 100 |
| Sandalwood oil | 100 |
| Hydroxycitronellal | 80 |
| Ethylene brassylate | 30 |
| Linalool | 30 |
| Eugenol extra | 10 |
| Cyclamen aldehyde | 10 |
| Phenylethyl alcohol | 100 |
| Methyl dihydrojasmonate | 100 |
|  | 960 |

When 40 parts of 1 are added to this flowery composition, then the resulting base is fresh-flowery, much milder, "cleaner" and is very suitable for modern, youthful lines.

On the other hand, by the addition of 40 parts of 8-methylmegastigma-5(11),8-dien-4,7-oxide 7 the composition is much heavier, sweeter and has a pronounced carnation note.

The addition of 40 parts of 2 confers to the composition a pleasant spicy and rose-like note which acets fresh and lively.

By the addition of 40 parts of 8 the composition is altered in a generally flowery direction, surprisingly in a rose direction.

EXAMPLE 25

Perfume composition (chypre direction) containing megastigma-5(11),8-dien-4,7-oxides [1, 5, 7 or 14]

|  | Parts by weight |
| --- | --- |
| Methyl 1-methylcyclododecyl ether | 200 |
| α-Hexylcinnamaldehyde | 200 |
| Bergamotte oil | 200 |
| Methyl dihydrojasmonate | 80 |
| Vetiveryl acetate | 60 |
| α-Ionone | 20 |
| Coriander oil | 20 |
| Benzyl acetate | 20 |
| Rhodinol | 20 |
| Ethylene brassylate | 20 |
| 8α,12-Oxido-13,14,15,16-tetranorlabdane | 10 |
| Wormseed oil | 10 |
| p-Menthane-8-thiol-3-one | 10 |
| 3,5-Dimethylcyclohex-3-en-1-ylcarboxaldehyde (10% in propyleneglycol) | 10 |
| Tree moss absolute (50% in propyleneglycol) | 20 |
| Patchouli oil | 20 |
|  | 920 |

When 80 parts of megastigma-5(11),8-dien-4,7-oxide 1 are added to this chypre composition, there is obtained a very pleasing spicy-herby, and at the same time also flowery, top note which is very suitable for use in modern perfumery (masculine lines).

By the addition of 80 parts of 2-methyl-megastigma-5(11),8-dien-4,7-oxide 5 there is obtained a very pleasant warm, soft precious wood note which is very much in demand in luxury perfumes. The composition has a very elegant note.

By the addition of 40 parts of 8-methyl-megastigma-5(11),8-dien-4,7-oxide 7 the composition becomes substantially more woody and also fresher and more spicy. It is suitable for masculine notes.

The addition of 40 parts of 10-methyl-megastigma-5(11),8-dien-4,7-oxide 14 leads in the direction of the warm, fine-woody chypre, but with substantially more diffusion than is the case in the original composition.

EXAMPLE 26

Perfume composition (tobacco direction) containing megastigma-5(11),8-dien-4,7-oxides [1, 14 or 7]

|  | Parts by weight |
|---|---|
| α-Ionone | 200 |
| o-Tert.butylcyclohexyl acetate | 200 |
| α-Hexyl-cinnamaldehyde | 110 |
| Musk ketone | 100 |
| Sandalwood oil | 100 |
| Styrallyl acetate | 60 |
| Methyl dihydrojasmonate | 60 |
| Coumarin | 20 |
| Benzoin resinoid | 20 |
| Isobutylquinoline (10% in propyleneglycol) | 20 |
| Lavander oil | 20 |
| Vetiver oil Bourbon | 10 |
| Melilotus absolute colourless | 10 |
| Galbanum oil | 10 |
|  | 940 |

With the addition of 6% of 1, the foregoing composition takes on a very original top note which is substantially fresher. The thus-obtained composition is suitable for modern tobacco notes (e.g. in masculine lines). On the other hand, by the addition of 6% of 10-methyl-megastigma-5(11),8-dien-4,7-oxide 14 there is produced the typical odour of the classical "tobacco perfumery". The novel composition is much warmer, fuller and has a typical tobacco character.

With the addition of only 2% of 8-methyl-megastigma-5(11),8-dien-4,7-oxide 7 there is obtained a rather woody, very fresh composition which is excellently suitable for masculine lines.

EXAMPLE 27

Fruity perfume base containing 2-methyl-megastigma-5(11),8-dien-4,7-oxide 5

|  | Parts by weight |
|---|---|
| Ethyl phthalate | 370 |
| Methyldihydrojasmonate | 200 |
| [4-(4-Methyl-3-pentenyl)-3-cyclohexen-1-yl]-methyl acetate | 120 |
| Cyclamen aldehyde | 80 |
| 2,6-Dimethyl-6-hepten-1-al (10% in propyleneglycol) | 60 |
| 2-Methyl-1,3-dioxolan-2-ethyl acetate | 60 |
| cis-6-Nonenol (10% in propyleneglycol) | 40 |
| cis-3-Hexenyl acetate (10% in propyleneglycol) | 20 |
| Lemon oil | 20 |
|  | 970 |

The addition of 30 parts of 5 confers to the fruit base much more naturalness. The melon character is intensified and the sweet-fruity note comes into play better.

EXAMPLE 28

Green perfume base containing 2-methylmegastigma-5(11),8-dien-4,7-oxide 5

|  | Parts by weight |
|---|---|
| Methyl dihydrojasmonate | 300 |
| Bergamotte oil | 300 |
| α-Hexylcinnamaldehyde | 200 |

-continued

|  | Parts by weight |
|---|---|
| Basil oil | 40 |
| Linalyl anthranilate | 20 |
| 3,5-Dimethylcyclohex-3-en-1-ylcarboxaldehyde (10% in propyleneglycol) | 20 |
| p-Menthane-8-thiol-3-one | 10 |
| Galbanum oil | 10 |
| Propyleneglycol | 20 |
|  | 920 |

The somewhat hard-green base takes on a much more natural tone after the addition of 80 parts of 5. The composition is decidedly reminiscent of the odour prevailing in a flower shop or in a hothouse. The complex is soft, round, like young leaves and reminiscent of bright "green".

EXAMPLE 29

Raspberry flavour containing megastigma-5(11),8-dien-4,7-oxide 1

|  | Parts by weight |
|---|---|
| cis-3-Hexenol | 0.15 |
| Methyl anthranilate | 0.15 |
| 4-(p-Hydroxyphenyl)-2-butanone | 0.5 |
| Dimethyl sulphide | 0.15 |
| Citral | 0.1 |
| Diethyl succinate | 1.5 |
| γ-Undecalactone | 1.5 |
| Celery seed oil | 1.0 |
| Anethol | 2.0 |
| Ethyl isovalerate | 2.5 |
| Ethyl α-methylphenylglycidate | 3.0 |
| Vanillin | 4.0 |
| Ethyl acetate | 6.0 |
| Jasmine absolute (10% in ethanol) | 2.0 |
| β-Ionone | 50.0 |
| Ethanol | 915.45 |
|  | 990.0 |

By the addition of 10 parts of a 1% solution of 1 in ethanol, the foregoing raspberry flavour is modified in an advantageous manner. Odourwise and flavourwise there now appears the delicate woody-fresh, pronounced fruity-sweet note which is characteristic of ripe raspberries.

EXAMPLE 30

Tea flavour containing megastigma-5(11),8-dien-4,7-oxide 1

|  | Parts by weight |
|---|---|
| Isovaleraldehyde | 0.5 |
| Camphor (10% in ethanol) | 0.5 |
| Geraniol (10% in ethanol) | 1.0 |
| Vanillin | 1.0 |
| Linalyl acetate (1% in ethanol) | 2.0 |
| Linalool | 2.0 |
| Butyl alcohol | 2.0 |
| Citral (1% in ethanol) | 3.0 |
| Tannin (5% in water) | 100.0 |
| Propyleneglycol | 838.0 |
|  | 950.0 |

When this tea base is treated with 50 parts of a 1% solution of 1 in ethanol, there is immediately established an advantageous modification. Odourwise and flavourwise the woody, herby-fresh note which is characteristic of black tea appears distinctly.

EXAMPLE 31

Megastigma-5(11)-8-dien-4,7-oxide 1 as a tobacco additive 100 g of Maryland tobacco were sprayed evenly with 4 ml of a 1% solution of 1 in ethanol and subsequently stored at room temperature for 24 hours. The cigarettes prepared from the thus-treated tobacco showed, upon smoking, a pleasant cooling effect. The smoke possessed an original fruity-flowery aspect; it was significantly milder and more pleasant than the smoke of untreated blind samples.

EXAMPLE 32

2-Methylmegastigma-5(11),8-dien-4,7-oxide 5 as a tobacco additive 100 g of Maryland tobacco were treated as described in Example 31 with 4 ml of a 1% solution of 5 in ethanol. The cigarettes prepared from the thus-treated tobacco showed, upon smoking, a very pleasant, significantly softer flavour than the corresponding blind samples.

I claim:

1. A compound of the formula:

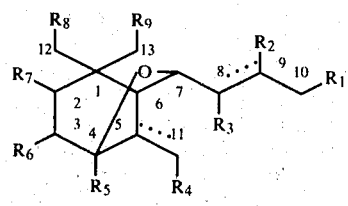

wherein:
(a) $R_1$ and $R_2$ represent a hydrogen atom or a methyl, propyl, vinyl, propenyl or allyl group;
(b) $R_3, R_4, R_5, R_6, R_7, R_8$ and $R_9$ each represent a hydrogen atom or a methyl or ethyl group;
(c) the dotted lines represent an optional bond when $R_1$ and/or $R_2$ is hydrogen, methyl or propyl and an obligatory bond when $R_1$ and/or $R_2$ represents a propenyl, vinyl or allyl group,; and
(d) the 5,11-bond is only saturated when the remainder of the molecule is saturated; excepting those natural mixtures containing megastigma-5(11),8-dien-4,7-oxide.

2. A compound in accordance with claim 1 having the formula:
megastigma-5(11),8-dien-4,7-oxide.

3. A compound in accordance with claim 1 having the formula:
8-methyl-megastigma-5-(11),8-dien-4,7-oxide.

4. A compound selected from the group consisting of 10-methyl-megastigma-5(11),8-dien-4,7-oxide; 10-allyl-megastigma-5(11),8-dien-4,7-oxide; 11-methyl-megastigma-5(11),8-dien-4,7-oxide; 4,11-dimethyl-megastigma-5(11),8-dien-4,7-oxide; 12/13-methyl-megastigma-5(11),8-dien-4,7-oxide and 2-methyl-megastigma-5(11),8-dien-4,7-oxide.

5. A compound of the formula:

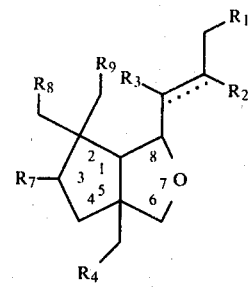

wherein:
(a) $R_1$ and $R_2$ represent a hydrogen atom or a methyl, propyl, vinyl, propenyl or allyl group;
(b) $R_3, R_4, R_7, R_8$ and $R_9$ represent a hydrogen atom or a methyl or ethyl group; and
(c) the dotted lines represent an optional bond when $R_1$ and/or $R_2$ is hydrogen, methyl or propyl and an obligatory bond when $R_1$ and/or $R_2$ represents a propenyl, vinyl or allyl group,.

6. A compound in accordance with claim 5, having the formula:
2,2,5-trimethyl-8-[prop-1'-enyl]-7-oxa-bicyclo[3.3.0]-octane.

7. A compound in accordance with claim 5, having the formula:
2,2,5-trimethyl-8-[1'-methyl-prop-1'-enyl]-7-oxa-bicyclo[3.3.0]-octane.

8. A process for the manufacture of compounds of the general formula:

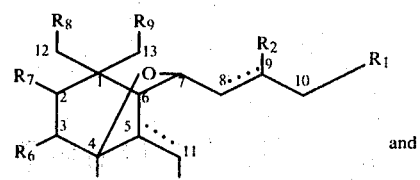

I and

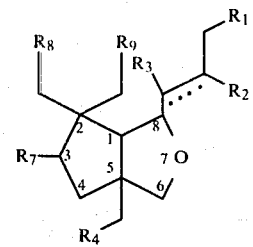

II wherein $R_1$ and $R_2$ represent a hydrogen atom or a methyl, propyl, vinyl, propenyl or allyl group and $R_3$, $R_4$, $R_5$, $R_6$, $R_7$, $R_8$ and $R_9$ represent a hydrogen atom or a methyl or ethyl group and the dotted lines represent an optional bond or, when $R_1$ and/or $R_2$ represent a propenyl, vinyl or allyl group, an obligatory bond, and the 5,11-bond in formula I is only saturated when the remainder of the molecule is saturated, which process comprises treating a compound of the general formula:

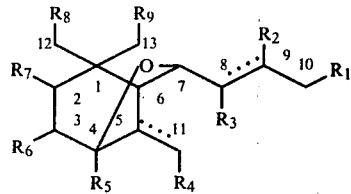

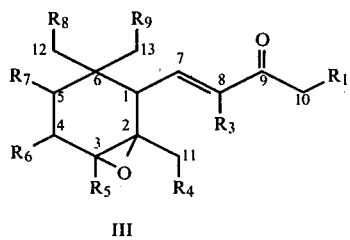

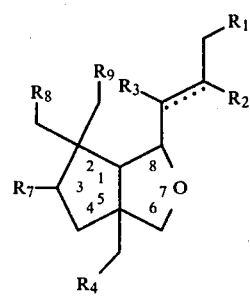

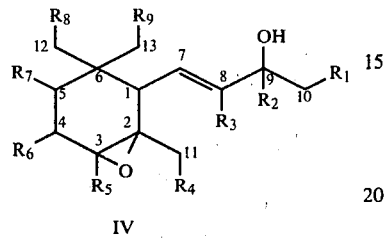

and from about 0.5% to 20.0% of a compound of the formula:

wherein $R_1$ to $R_9$ have the significance given earlier in this claim, with an aluminium sec.alcoholate, the treatment being carried out under reducing conditions when a compound of formula III is used, and, if desired in optional sequence, separating the resulting mixture of the compounds of formulae I and II into the components and hydrogenating $C{=}C$ bonds which may be present in the compounds of formulae I and II.

9. A process according to claim 8, wherein aluminium isopropylate is used as the aluminium sec.alcoholate.

10. A composition consisting essentially of from about 80.0% to 99.5% of a compound of the formula:

wherein:
(a) $R_1$ and $R_2$ represent a hydrogen atom or a methyl, propyl, vinyl, propenyl or allyl group;
(b) $R_3, R_4, R_5, R_6, R_7, R_8$ and $R_9$ each represent a hydrogen atom or a methyl or ethyl group;
(c) the dotted lines represent an optional bond when $R_1$ and/or $R_2$ is hydrogen, methyl or propyl, and an obligatory bond when $R_1$ and/or $R_2$ represents a propenyl, vinyl or allyl group; and
(d) the 5,11 double bond is only saturated when the remainder of the molecule is saturated.

11. A composition of claim 10 which consists essentially of megastigma-5(11),8-dien-4,7-oxide and 2,2,5-trimethyl-8(prop-1-enyl)-7-oxabicyclo[3.3.0]-octane in a ratio of about ten to one.

12. A composition of claim 10 which consists essentially of 8-methyl megastigma-5(11),8-dien-4,7-oxide and 2,2,5-trimethyl-8-(1-methylprop-1-enyl)-7-oxabicyclo[3.3.0]octane in a ratio of about 9 to 1.

* * * * *